United States Patent [19]
Smith

[11] Patent Number: 4,973,328
[45] Date of Patent: Nov. 27, 1990

[54] CLOSED SYSTEM ADMINISTERING ASSEMBLY

[76] Inventor: Gerard Smith, 9363 Fontainebleau Blvd., #203, Miami, Fla. 33172

[21] Appl. No.: 438,050

[22] Filed: Nov. 20, 1989

[51] Int. Cl.$^5$ .............................................. A61B 19/00
[52] U.S. Cl. .................................... 604/411; 604/256; 604/905; 604/111; 604/244
[58] Field of Search ............... 604/411, 412, 413, 414, 604/415, 905, 256, 244, 111

[56] References Cited
U.S. PATENT DOCUMENTS

| | | | |
|---|---|---|---|
| 4,731,061 | 3/1988 | Matkovich | 604/256 X |
| 4,798,605 | 1/1989 | Steiner et al. | 604/411 |
| 4,915,704 | 4/1990 | Miyasaka et al. | 604/905 X |

*Primary Examiner*—John D. Yasko
*Attorney, Agent, or Firm*—Malloy, Downey & Malloy

[57] ABSTRACT

An assembly for the administering of liquid, such as medicines, saline solutions, etc. intravenously to a patient incorporating a sterile, closed system specifically designed for set-up and use by a patient in a domestic environment and in situations where the patient administers fluid to himself with a minimum of medical personnel supervision or aid.

14 Claims, 3 Drawing Sheets

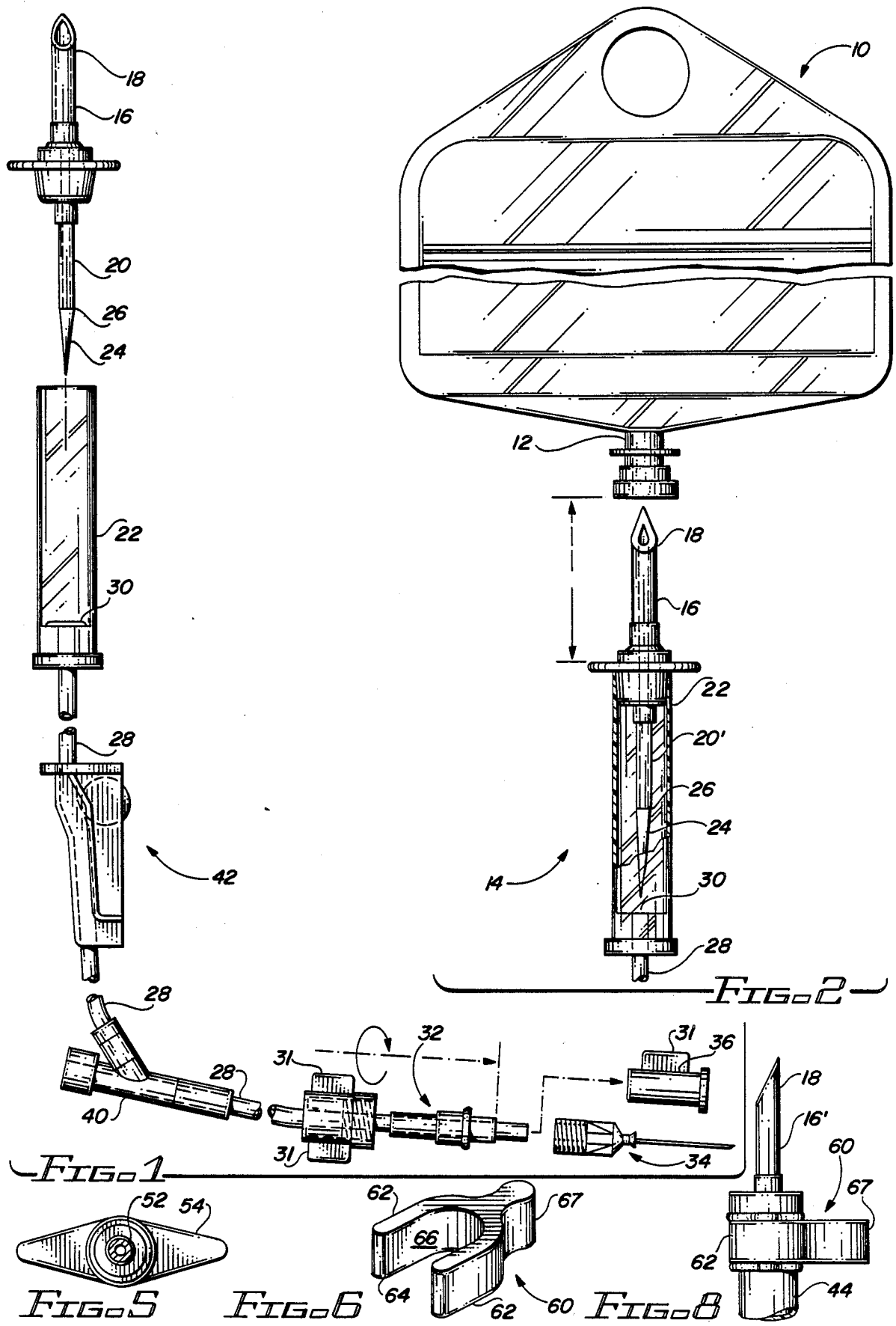

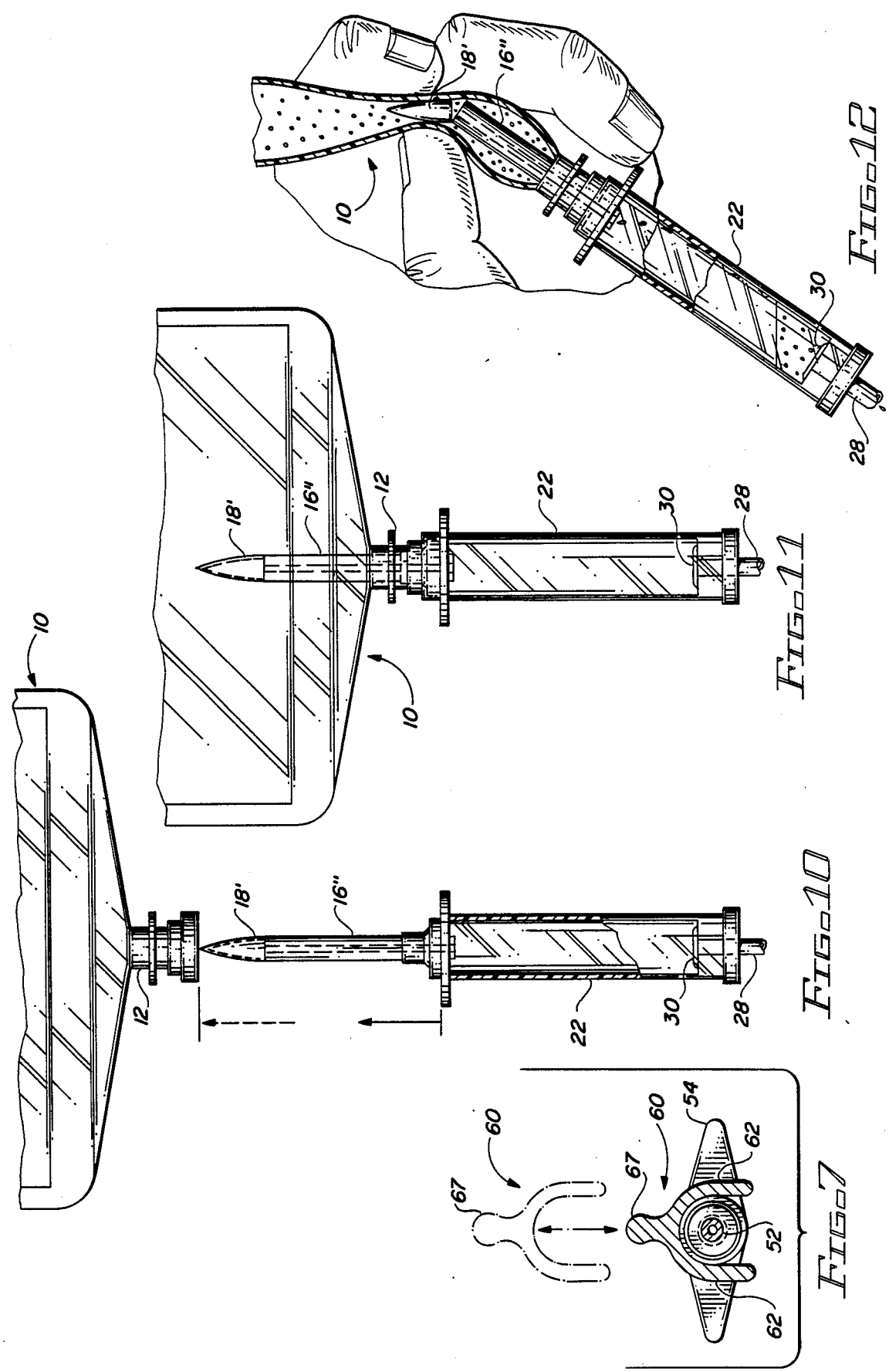

CLOSED SYSTEM ADMINISTERING ASSEMBLY

BACKGROUND OF THE INVENTION

1. Field of the Invention

This invention relates to a closed system liquid administering assembly for the infusion of liquids from a liquid supply container intravenously to the patient wherein the assembly maintains a closed, sterile administering system enabling the patient to first connect the system to an infusion device such as a catheter or the like and subsequently, opening a path of fluid flow within a sealed chamber between the liquid to be administered and the infusion device applied to the patient.

2. Description of the Prior Art

In the medical profession, it is common practice to deliver fluid to a patient intravenously using a patient applied catheter or like infusion device further wherein an elongated flexible material delivery tube is attachable by some applicable device to a fluid supply container structured for hanging in depending and supporting relation on an I.V. pole. The liquid flow is delivered to the patient by gravity. When such systems are "set-up" by medical personnel within a hospital or like environment, care is taken by the personnel to maintain a closed system if possible and insure that the administering of fluid to the patient is accomplished under as sterile conditions as possible.

However, in many situations, a patient is intended to have such fluids applied or administered in his own home or in an environment other than a hospital or the like with minimum supervision by medical personnel. In some situations, the patient is expected to accomplish "setting-up" of the delivery or administering system himself. Problems exist with this latter situation in that it is sometimes difficult, due to the patient's ineptitude or negligence to maintain a closed administering assembly and a sterile environment.

Fluid administering systems do exist wherein the patient is expected to apply a delivery tube to the interior of a fluid supply container as well as securing the opposite or proximal end of the delivery tube to an infusion device attached to the patient. The manner in which the above is accomplished frequently results in an opening of the administering apparatus to atmosphere thereby allowing the fluid to be administered in a less than totally sterile environment.

Various apparatus and/or systems associated with prior art administering assembly include U.S. Pat. No. 2,894,510; 4,340,049 and 4,586,928. In addition to the above, a connecting or attachment apparatus is also commercially available and in wide use in many of the applications as set forth above.

Even in light of the above, there is still a demand and need for a fluid administering system whereby liquid is administered in a closed system and resulting sterile environment in a manner which simplifies and reduces the effect of patient neglect or ineptitude in accomplishing such administration.

SUMMARY OF THE INVENTION

The present invention relates to a liquid administering assembly which is specifically structured to define a closed system in that the liquid to be administered is isolated from the atmosphere. Sterile conditions under which liquid is administered, intravenously, to the patient are thereby maintained and such structure is specifically adapted for utilization by the patient with a minimum amount of supervision from medical personnel, such as when the patient self-administers fluids in the home.

The subject assembly comprises a liquid supply container wherein the liquid to be administered is maintained on the interior thereof. An elongated flexible material delivery tube well known in the medical profession has a proximal end attached in fluid communication to the supply container and a distal end having an adaptor structure mounted thereon for inter-connection and fluid communication with an infusion device attached intravenously to the patient.

An important feature of the present invention is the sealed inter-connection of the various components, to be described in greater detail hereinafter, which maintains the entire administration system and the delivery of the liquid under a sterile environment through the maintenance of a closed system. More specifically, the proximal end of the elongated delivery tube is secured to the supply container by a mounting means. The mounting means includes a flexible material chamber having a hollow interior connected in sealed engagement with the proximal end of the delivery tube and also in sealed engagement with the liquid supply container and/or with an access orifice considered to be a part thereof. The mounting means further comprises an elongated delivery conduit having an inner end disposed on the interior in direct fluid communication with the liquid container therein. The delivery conduit has an outer end protruding outwardly from the interior of the supply container. The outer end is initially sealed in a closed condition and thereby segregated from the interior of the chamber. However, the outer end includes a frangible portion which, upon the application of certain force thereto, will separate from the remainder of the outer end of the delivery conduit thereby establishing a clear path of liquid flow from the interior of the supply container to the interior of the chamber. The interior of the chamber, set forth above, is connected in sealed relation to the proximal end thereby allowing the liquid to be administered to freely pass, under gravity flow, from the interior of the supply container directly to the proximal end of the delivery tube and along the length thereof. The gravity flow will cause the liquid administered to pass through the infusion device which is initially connected to the adaptor structure secured to the distal end of the delivery tube and eventually, into the patient through intravenous technique.

An important feature of this invention is the formation of the chamber from a flexible material wall portion wherein such wall portion may be deformed so as to effectively apply force sufficient to break or separate the frangible portion of the outer end of the delivery conduit thereby opening the outer end and allowing the fluid to pass into the interior of the chamber, as set forth above.

Another embodiment of the present invention comprises the chamber including a wall portion structured to be longitudinally collapsible when an externally applied stop element is removed from its stopping engagement relative to the chamber. More specifically, the aforementioned wall portion of this embodiment of the present invention may have a bellowed or longitudinally collapsible wall structure which allows relative displacement between the outer end of the delivery conduit and an internally mounted sealing diaphragm disposed within the interior of the chamber. Such diaphragm is disposed to seal off and segregate communication between the proximal end of the delivery tube and the outer end of the delivery conduit. However, forcing of the longitudinally collapsible wall portion of the chamber into its collapsed position will force the outer end of the delivery conduit into abutting, penetrating relation to the diaphragm and more particularly, to a frangible portion integrally formed thereon. Such abutting engagement of the outer end will serve to penetrate or open the sealing or segregating diaphragm thereby allowing fluid communication between the outer end of the delivery conduit and the proximal end of the delivery tube.

A path of fluid flow will thereby be established between the liquid on the interior of the supply container and the proximal end of the delivery tube so as to allow liquid to flow along the length of the delivery tube to the distal end thereof and to the infusion device secured to the adaptor structure mounted on the distal end of the delivery tube.

BRIEF DESCRIPTION OF THE DRAWINGS

For a fuller understanding of the nature of the present invention, reference should be had to the following detailed descriptions taken in connection with the accompanying drawings in which:

FIG. 1 is a longitudinal exploded view of the various components of one embodiment of the present invention.

FIG. 2 is a front plan view in partial cut-away showing details of one component of the present invention.

FIG. 5 is an end view in part in section taken along line 5—5 of FIG. 4.

FIG. 6 is a perspective view of a locking member associated with the embodiment of FIG. 4.

FIG. 7 is a sectional view in partial phantom along line 7—7 of FIG. 4.

FIG. 8 is an end view along line 8—8 of FIG. 4.

FIG. 10 is a front view in partial cut-away of yet another embodiment of the present invention.

FIG. 11 is a front view in partial cut-away of the embodiment of FIG. 10 at an operative position.

FIG. 12 is an embodiment of FIG. 10 and 11 in further detail.

Like reference numerals refer to like parts throughout the several views of the drawing.

BRIEF DESCRIPTION OF THE PREFERRED EMBODIMENT

Figure 3:
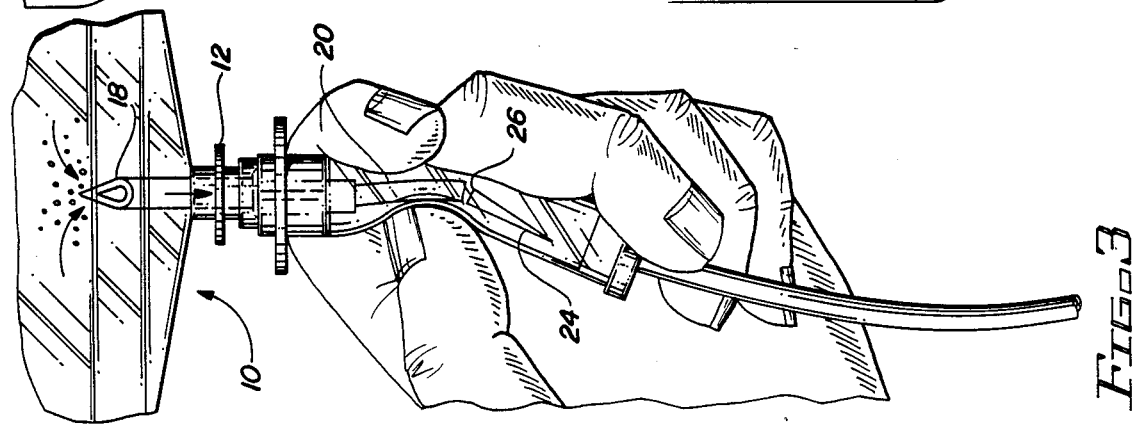
FIG. 3 shows an exterior view of the component shown in detail in FIG. 2.

As shown in FIGS. 1 through 3, a preferred embodiment of the present invention comprises a liquid supply container generally indicated as 10 including an access structure or receptor as at 12 communicating with the interior of the container and the fluid contained therein. A mounting means generally indicated as 14 and shown in detail in FIGS. 1, 2 and 3 is structured for inter-connection into the interior of the supply container 10. The mounting means is further structured to allow passage of the fluid contained therein through a delivery conduit 16 having a proximal end 18 and a distal end 20. The proximal end is designed to pass through the receptor 12 so as to establish fluid flow with the interior of the supply container 10. The mounting means 14, however, further includes an elongated and hollow chamber 22 having a cylindrical, flexible material wall disposed in surrounding and enclosing relation to the distal end 20 of the delivery conduit 16.

The distal end 20 of delivery conduit 16 is further structured by a separable, frangible portion as at 24 connected to the distal end 20 by a weakened junction line as at 26. Sufficient force placed on the frangible portion 24 will cause a rupturing at the junction line 26 and will allow fluid or liquid to pass from the interior of the supply container 10 through the interior length of the delivery conduit 16 to the interior of the flexible material chamber 22. The interior of the chamber 22 communicates with a flexible material, elongated delivery tube 28 through a proximal end thereof as at 30 communicating directly with the interior of the chamber 22. Once the frangible portion 24 has been separated, as clearly shown in FIG. 3, fluid communication throughout the entire system including along the length of the delivery tube 28 is established.

Again with reference to FIG. 3, the cylindrical wall from which the chamber 22 is formed has sufficient flexibility to allow a person's hand to grippingly engage the proximal end 20 of the delivery conduit 16 even though it is encased within the chamber 22. The application of sufficient force to the frangible end as at 24 will cause the aforementioned severing at the weakened junction 26, thereby allowing liquid to flow into the interior of the chamber 22 and eventually, through the length of the delivery tube 28. The opposite or distal end of the delivery tube 28 has an adaptor means as at 32 affixed thereto. This adaptor means 32 is specifically structured for fluid inter-connection to an infusion device such as a catheter or the like generally indicated as 34. A protective cap such as at 36 may enclose the operative end of the adaptor means 32 until it is ready or inter-connection to the infusion device or catheter 34. Other relatively conventional structures may be incorporated along the length of the tube 28. Such components may include a Y-type connector 40 for the addition of fluid along the length of the tube to the infusion device 34 and the patient to which it is connected. Further, a cut-off valve or like structure generally indicated as 42 may also be mounted as desired along the length. In order to facilitate handling of the various components, gripping wings or outwardly extending flanges as at 31 may be added as shown.

Figure 9:
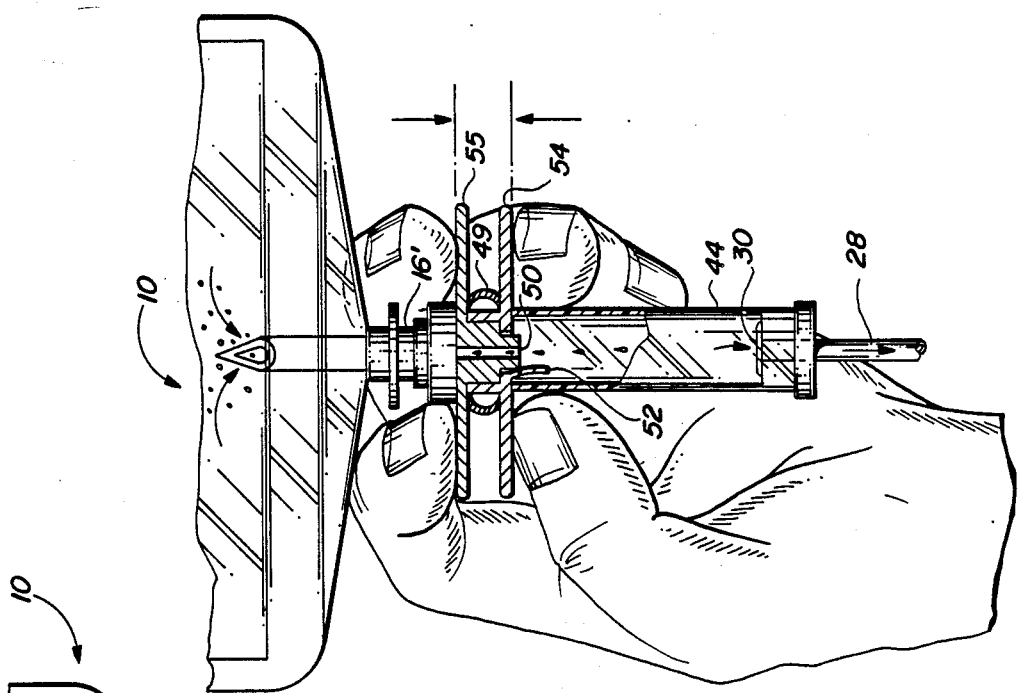
FIG. 9 is a longitudinal sectional view in partial cut-away showing the structure of the embodiment of FIG. 4 forced into its operative liquid flowing position.
Figure 4:
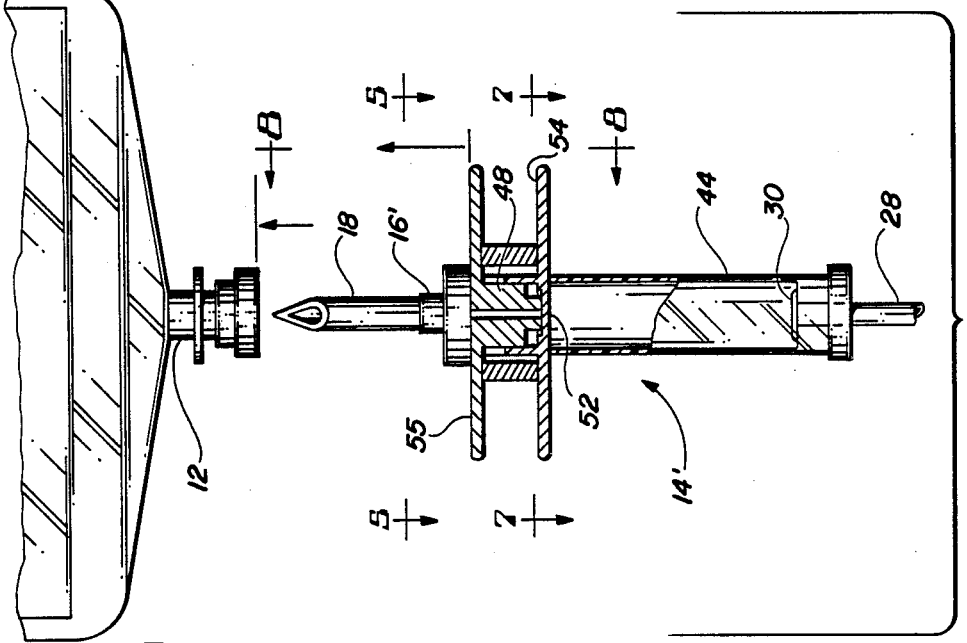
FIG. 4 is a longitudinal sectional view in partial cut-away of yet another embodiment of the present invention.

With reference to FIGS. 4 through 9, a second preferred embodiment of the present invention is also designed for inter-connection to a supply container 10 by an access opening surrounded or connected to a receiving receptor 12 and including a mounting means generally indicated as 14'. The mounting means in the present invention also includes a flexible material chamber as at 44 connected at one end to the proximal end as at 30 of the delivery tube 28. As shown best in FIGS. 4 and 9, the mounting means further includes a delivery conduit 16' having a proximal end 18 protruding outwardly from the corresponding end of the chamber 44 so as to pass through the receptor structure 12 and into the interior of the supply container 10 to establish fluid communication with the liquid maintained therein. However, a portion of the chamber 44 has a segment as at 48 which is capable of longitudinal collapse or displacement as best seen in FIG. 9. Such displacement may take place by a bellows or like configuration or an otherwise outwardly or inwardly bowing segment as at 49 of the flexible section 48. When such occurs, a distal end of the delivery conduit 16' as at 50 will force a frangible portion as 52 outwardly from its normally liquid tight or sealed engagement as shown in FIG. 4. The frangible disk 52 or like member may be secured to the plate 54 on the interior of the chamber 44 by an annularly or at least partially circular weakened junction line. Accordingly, a downward or axial force applied to the frangible portion 52 will cause its partial severance and an opening or communicating inter-connection with the interior of the delivery conduit 16' by the distal end thereof 50 forcing its way through the newly formed aperture after displacement of the frangible portion 52 has occurred. Liquid will therefor pass from the interior of the container 10 into the interior of the chamber 44 and from there into and throughout the length of the delivery tube 28. The proximal end of the delivery tube 28 as at 30 communicates directly with the interior of the chamber 44 to establish such fluid communication and liquid flow.

In order to prevent inadvertent opening of fluid flow, a locking or blocking member generally indicated as 60 is provided. Such blocking member may have a U-shaped configuration including two parallel, spaced apart leg portions 62 having an open end as at 64. The space between the leg 62 as at 66 is sufficient to allow the legs 62 to effectively straddle the segment 48 of the chamber 44 which is structured for longitudinal displacement or collapse as described with reference to FIG. 9. Once the blocking member 60 has been removed from its blocking position as indicated in the phantom lines of FIG. 7, the two flange member 54 and 55 may be positioned closer to one another as shown in FIG. 9 by application of a gripping force by the fingers of the users as clearly shown in FIG. 9.

In order to facilitate removal of the blocking member 60 from its blocking or separating position relative to flanges 54 and 55, a handle or outwardly protruding knob or the like as at 67 may be disposed to facilitate easy gripping of the blocking member 60.

Yet another embodiment of the present invention is shown in FIGS. 10, 11 and 12 wherein a closed system is maintained but the structure is more specifically defined the delivery conduit 16" having an initially closed or sealed frangible end 18'. The entire system may be delivered to patient or ultimate consumer by lockingly engaging or fixedly inserting the conduit 16" in the interior cf the supply container 10 with the frangible end portion 18' maintained in its sealed position.

Due to the flexibility of the material from which the supply container 10 is formed, activation of the system occurs by one using his hands to detach the frangible end 18' from the delivery conduit 16" so that the fluid within the supply container 10 may pass into the hollow chamber 22. Further, in this embodiment, the chamber 22 need not necessarily be made of a flexible material since there is no need to break any frangible end or conduit portion disposed therein as in the embodiment of FIG. 1. Also, the hollow chamber 22 may be of a much shorter length and/or the delivery end of the delivery conduit 16" communicating with the interior of the hollow chamber 22 as shown in FIGS. 10, 11 and 12 may in fact be more directly connected to the tube 28.

It should be readily apparent therefore, that in any of the embodiments described with the present invention, a closed system is maintained until the distal end of the delivery tube, through the adaptor means 32, is applied to the infusion device or catheter as at 34. Once the distal end of the delivery tube 28 is so connected, the mounting means is effectively "opened" and fluid is allowed to pass in a closed system upon the separation of the frangible portion from the distal end of the delivery conduit thereby allowing the liquid within the supply container 10 to pass into the interior of the flexible wall chamber as described with regard to each of the subject embodiments.

Now that the invention has been described,
What is claimed is:
1. An administering assembly for delivering liquid to a patient intravenously through a catheter or like medical infusion device, said assembly comprising, in combination:
 (a) a supply container including liquid maintained on the interior thereof,
 (b) an elongated delivery tube formed of a flexible material and including a distal end attached to the infusion device and an oppositely disposed proximal end,
 (c) a mounting means connected to both said proximal end and to said supply container for delivering the liquid from the interior of said supply container to said proximal end,
 (d) a delivery conduit having an inner end disposed on the interior of said supply container in communicating relation with the liquid therein, and an outer, initially sealed end protruding outwardly from the supply container,
 (e) said mounting means further comprising a hollow interior, flexible material chamber sealed between said supply container and said proximal end in surrounding relation to said outer end of said delivery conduit, said chamber defining a path of fluid communication between said delivery tube and said proximal end when said outer end of said delivery conduit is open,
 (f) said initially sealed outer end including a frangible portion separable from a remainder thereof, said outer end defining a path of liquid flow between the interior of said supply container and the interior of said chamber and the proximal end of the delivery conduit upon opening of said outer end, and
 (g) said supply container, mounting means and delivery tube defining a sealed, closed liquid delivery system when said outer end of said delivery conduit is in its initially sealed condition.

2. An assembly as in claim 1 wherein said distal end includes an adaptor means structured for fluid flow communication to the infusion device.

3. An assembly as in claim 2 further comprising a Y-type connection formed along the length of said delivery tube and normally sealed to atmosphere and structured to add liquid to the interior of said delivery tube downstream of said supply container.

4. An assembly as in claim 3 further comprising a valve means mounted on said delivery tube and structured for regulation of fluid flow from said supply container to said distal end of said delivery tube.

5. An assembly as in claim 1 wherein said chamber includes a wall portion formed of flexible material and being of sufficient flexibility to allow deformation cf said wall portion and the application of a breaking force on said frangible portion of said outer end of said delivery conduit.

6. An assembly as in claim 5 wherein said frangible portion is disposed within said chamber and maintained on the interior thereof when separated from the remainder of said outer end of said delivery conduit.

7. An assembly as in claim 1 wherein said chamber includes a wall portion structured for longitudinal collapse, said outer end positionable into and out of abutting, displaceable engagement with a sealing diaphragm and into fluid communication with said proximal end and upon longitudinal collapse of said wall portion.

8. An assembly as in claim 7 further comprising a stop member removably secured to said chamber in cooperative relation to said wall portion and disposed and structured to prevent longitudinal collapse of said wall portion or longitudinal displacement of said outer end and said sealing diaphragm relative to one another.

9. An assembly as in claim 8 wherein said stop member comprises a substantially U-shaped yolk structure removably mounted in at least surrounding relation to said collapsible wall portion.

10. An assembly as in claim 9 wherein said sealing diaphragm is disposed on the interior of said chamber in sealing, fluid segregating relation between opposite ends of the interior of said chamber and between said proximal end of said delivery tube and said outer end of said delivery conduit.

11. An assembly as in claim 10 wherein said diaphragm comprises a frangible portion separable, at least in part, from a remainder of said diaphragm and disposed in aligned, interruptive relation with the longitudinal displacement of said outer end of said delivery conduit upon longitudinal collapse of said wall portion of said chamber.

12. An assembly as in claim 7 wherein said wall portion comprises a bellows configuration capable of longitudinal movement between a collapsed and a outwardly extended position.

13. An administering assembly for delivering liquid to a patient intravenously through a catheter or like medical infusion device, said assembly comprising, in combination:

a. a supply container including liquid maintained on the interior thereof,
 b. an elongated delivery tube formed of a flexible material and including a distal end attached to the infusion device and an oppositely disposed proximal end,
 c. a mounting means connected to both said proximal end and to said supply container for delivering the liquid from the interior of the supply container to said proximal end,
 d. said mounting means comprising a hollow interior chamber mounted between said supply container and said proximal end, said chamber defining a path of fluid communication between the supply container and said proximal end,
 e. a delivery conduit having a closed, sealed end and an open end and connected to both said supply container and said chamber and disposed at least partially on an interior of said supply container to define a path of liquid flow from the supply container to said chamber,
 f. said closed end of said delivery conduit including a frangible portion separable from a remainder of said delivery conduit and thereby establishing flow of liquid between the interior of said supply container and the interior of said chamber upon separating said frangible portion from the remainder of said delivery conduit, and
 g. said supply container, chamber and delivery tube defining a sealed, closed liquid delivering system when said closed end of said delivery conduit is in its initially sealed condition.

14. An assembly as in claim 13 wherein said closed end and said frangible portion of said delivery conduit is disposed on the interior of said supply container and defines an inner end of said delivery conduit, said open end of said delivery conduit defining an outer end thereof and mounted in adjacent, direct communication with the interior of said chamber, said frangible portion separable from the remainder of said delivery conduit on the interior of said supply container to define liquid flow between the interior of said supply container and the interior of said chamber upon separating said frangible portion from the remainder of said delivery conduit.

* * * * *